(12) United States Patent
Norman et al.

(10) Patent No.: US 10,094,494 B2
(45) Date of Patent: Oct. 9, 2018

(54) FERRULE WITH FEATURES FOR SOFTENING FERRULE CRUSH AND RELATED METHODS

(71) Applicant: Agilent Technologies, Inc., Santa Clara, CA (US)

(72) Inventors: Wesley M. Norman, Santa Clara, CA (US); Wei J. Song, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 524 days.

(21) Appl. No.: 14/752,147

(22) Filed: Jun. 26, 2015

(65) Prior Publication Data

US 2016/0377203 A1 Dec. 29, 2016

(51) Int. Cl.
| | | |
|---|---|---|
| *F16L 13/14* | (2006.01) | |
| *F16L 21/08* | (2006.01) | |
| *A61M 39/00* | (2006.01) | |
| *F16L 19/065* | (2006.01) | |

(52) U.S. Cl.
CPC .............. *F16L 13/14* (2013.01); *A61M 39/00* (2013.01); *F16L 21/08* (2013.01); *F16L 19/065* (2013.01)

(58) Field of Classification Search
CPC ......... F16L 19/10; F16L 13/14; F16L 15/009; F16L 19/06; F16L 21/08; F16L 19/065; A61M 39/00; Y10T 29/49908

See application file for complete search history.

(56) References Cited

U.S. PATENT DOCUMENTS

| | | | |
|---|---|---|---|
| 2,287,889 A | 12/1940 | Krumsiek et al. | |
| 2,381,554 A | 8/1942 | Norgren | |
| 2,463,707 A | 7/1947 | Matousek | |
| 3,055,684 A | 9/1962 | Currie | |
| 3,229,341 A | 1/1966 | Maras | |
| 3,498,647 A | 3/1970 | Schroder | |
| 3,893,716 A | 7/1975 | Moreiras et al. | |
| 4,205,417 A | 6/1980 | Mackal | |
| 4,263,592 A | 4/1981 | Takahashi et al. | |

(Continued)

FOREIGN PATENT DOCUMENTS

| | | |
|---|---|---|
| WO | 2012/009726 A1 | 1/2012 |
| WO | 2014007820 A1 | 1/2014 |

OTHER PUBLICATIONS

Valco Instruments Co. Inc. VICI AGT International; Valco Fittings; http://www.vici.com/vfit/fs_intro.php (2014).

(Continued)

*Primary Examiner* — Carib A Oquendo

(57) ABSTRACT

A ferrule includes a body surrounding a bore that provides a fluid path along a central axis between a first end and a second end of the ferrule. The body includes a conical section configured for forming a sealing interface with a fitting in which the ferrule may be inserted and a sealing interface with a tube that may be inserted in the ferrule bore. The conical section includes collapse zones configured to collapse in a direction along the central axis in response to axial compression of the ferrule against the fitting. The collapse zones mitigate crushing of the ferrule against the tube. The collapse zones may be provided by a sealing region at the nose of the ferrule and annular grooves on the ferrule.

20 Claims, 11 Drawing Sheets

(56) References Cited

U.S. PATENT DOCUMENTS

| | | | |
|---|---|---|---|
| D262,397 S | 12/1981 | Ryan | |
| 4,586,731 A | 5/1986 | Castrup | |
| 4,890,867 A | 1/1990 | Briggs et al. | |
| 5,191,888 A | 3/1993 | Palmer et al. | |
| 5,288,113 A | 2/1994 | Silvis et al. | |
| 5,317,799 A | 6/1994 | Chapman et al. | |
| 5,328,160 A | 7/1994 | McLaughlin | |
| 5,381,497 A | 1/1995 | Toland et al. | |
| 5,390,269 A | 2/1995 | Palecek et al. | |
| 5,399,173 A | 3/1995 | Parks et al. | |
| 5,540,464 A | 6/1996 | Picha | |
| 5,595,406 A | 1/1997 | Warchol | |
| D383,053 S | 9/1997 | Schrader et al. | |
| D383,378 S | 9/1997 | Schrader et al. | |
| 5,669,637 A | 9/1997 | Chitty et al. | |
| 5,720,734 A | 2/1998 | Copenhaver et al. | |
| D398,935 S | 9/1998 | Chevalier | |
| 5,857,719 A | 1/1999 | Hansen | |
| 6,056,331 A | 5/2000 | Benett et al. | |
| 6,086,574 A | 7/2000 | Carroll et al. | |
| 6,102,449 A | 8/2000 | Welsh | |
| 6,131,963 A | 10/2000 | Williams et al. | |
| 6,152,885 A | 11/2000 | Taepke | |
| 6,220,635 B1 * | 4/2001 | Vitel | F16L 21/04 285/337 |
| 6,575,501 B1 | 6/2003 | Loy, Jr. | |
| 6,629,708 B2 | 10/2003 | Williams et al. | |
| 6,709,027 B2 | 3/2004 | Rittenhouse | |
| D497,300 S | 10/2004 | Chen | |
| 6,851,729 B2 | 2/2005 | Gibson | |
| 6,905,252 B2 | 6/2005 | Wisecarver | |
| 6,926,313 B1 | 8/2005 | Renzi | |
| 6,969,095 B2 | 11/2005 | Rittenhouse | |
| 6,981,720 B2 | 1/2006 | White et al. | |
| 7,048,448 B2 | 5/2006 | Rosenberg et al. | |
| 7,066,496 B2 | 6/2006 | Williams et al. | |
| 7,108,288 B2 | 9/2006 | Bennett et al. | |
| 7,118,290 B2 | 10/2006 | Ishigami et al. | |
| 7,316,777 B2 | 1/2008 | Loy, Jr. | |
| 7,367,595 B2 | 5/2008 | Williams et al. | |
| 7,527,436 B2 | 5/2009 | Hodge et al. | |
| 7,695,027 B2 | 4/2010 | Williams et al. | |
| 7,708,470 B2 | 5/2010 | Cooke et al. | |
| 7,735,878 B2 | 6/2010 | Keene | |
| 7,878,716 B2 | 2/2011 | Morgenstern | |
| D639,657 S | 6/2011 | Hoyt et al. | |
| D647,183 S | 10/2011 | Bertram | |
| 8,038,180 B2 | 10/2011 | Williams et al. | |
| 8,128,131 B2 | 3/2012 | Barnett et al. | |
| D670,776 S | 11/2012 | Fossum et al. | |
| 8,337,094 B2 | 12/2012 | Drake | |
| D676,126 S | 2/2013 | Hair | |
| D678,967 S | 3/2013 | Fossum et al. | |
| 8,783,486 B1 | 7/2014 | Hoyt et al. | |
| D711,328 S | 8/2014 | Purdy et al. | |
| D714,372 S | 9/2014 | Savill | |
| D722,364 S | 2/2015 | Reinhardt | |
| D735,853 S | 8/2015 | Pa | |
| 9,151,734 B2 | 10/2015 | Ellis et al. | |
| D775,326 S | 12/2016 | Shulman | |
| D777,903 S | 1/2017 | Schultz | |
| D783,815 S | 4/2017 | Lewis et al. | |
| 2005/0033269 A1 | 2/2005 | Decaria | |
| 2006/0169628 A1 | 8/2006 | Lay | |
| 2008/0025671 A1 | 1/2008 | Boutoussov et al. | |
| 2008/0054626 A1 | 3/2008 | Bearer et al. | |
| 2009/0295156 A1 | 12/2009 | Ford et al. | |
| 2010/0123309 A1 | 5/2010 | Miller et al. | |
| 2010/0123310 A1 | 5/2010 | Miller et al. | |
| 2010/0133806 A1 | 6/2010 | Barnett et al. | |
| 2010/0224546 A1 | 9/2010 | Ellis et al. | |
| 2011/0107823 A1 | 5/2011 | Dehmer | |
| 2011/0173798 A1 | 7/2011 | Miller et al. | |
| 2011/0303593 A1 | 12/2011 | Reinhardt | |
| 2013/0022317 A1 | 1/2013 | Norris et al. | |
| 2013/0043672 A1 | 2/2013 | Jeannotte et al. | |
| 2013/0147182 A1 | 6/2013 | Murphy et al. | |
| 2014/0178006 A1 | 6/2014 | Dunn et al. | |
| 2014/0375050 A1 | 12/2014 | Zeko et al. | |
| 2015/0036982 A1 | 2/2015 | Nhep et al. | |
| 2015/0145246 A1 | 5/2015 | Pa | |
| 2015/0284174 A1 | 10/2015 | Vogels et al. | |
| 2016/0377203 A1 | 12/2016 | Norman et al. | |

OTHER PUBLICATIONS

SilTite FingerTite; http://www.sge.com/products/gc--lc-supplies/gc-supplies;gc-ferrules3/siltite-fingertite; Trajan Scientific Australia Pty Ltd (2015).

FlexiMetal ferrule system for CFT devices; http://www.sge.com/products/gc--lc supplies/gc-ferrules/siltite-metal-ferrules3; Trajan Scientific Australia Pty Ltd (2015).

Ferrule Selection; SilTite Metal Ferrules; http://www.sge.com/support/training/injection/ferrule-selection; Trajan Scientific Australia Pty Ltd (2015).

.316 Stainless Steel Swagelok Tube Fittings; www.swagelok.com Oct. 2003.

IP.com Electronic Publication No. 000239661, "Soft Metal Ferrule with Improved Sealing", Nov. 2014.

Ex Parte Quayle Office action dated May 10, 2017 from related U.S. Appl. No. 29/594,829.

Final Office action dated Jun. 2, 2017 from related U.S. Appl. No. 29/531,557.

* cited by examiner

FERRULE WITH FEATURES FOR SOFTENING FERRULE CRUSH AND RELATED METHODS

TECHNICAL FIELD

The present invention relates generally to ferrules utilized to form leak-free fluidic connections between two conduits, and particularly to ferrules configured to soften ferrule crush and thereby prevent damage to tubes engaged by such ferrules.

BACKGROUND

Ferrules are utilized to form leak-free fluidic connections between two conduits. Ferrules are often employed in applications entailing small-scale fluid flows, such as analytical instruments and microfluidic devices, and thus may be sized to join small-bore conduits such as capillary tubing or fluidic fittings. As one example, a ferrule may be utilized to join the end of a capillary-scale chromatographic column to a fitting that is part of or communicates with an analytical detector or the sample inlet of an analytical measurement device containing a detector such as, for example, a mass spectrometer. Ferrules are typically monolithic articles composed of a metal, graphite, or a composite such as graphite-polyimide. The capillary tubes engaged by ferrules are often composed of fused silica with a polyimide coating. The body of a typical ferrule is axisymmetric and defines an internal bore through which the tube to be sealed is inserted. At least a portion of the ferrule, or "nose" portion, is often conical.

In a typical application, forming a fluidic seal entails inserting the capillary conduit through the ferrule and then inserting the ferrule and tube into the bore of a fluidic fitting. Alternatively, the ferrule may be inserted into the fitting bore first and the conduit then inserted into the ferrule. The ferrule is inserted far enough that a sealing region on the outside surface of the conical nose portion of the ferrule comes into contact with a conical inside wall of the fitting. The ferrule is then translated axially against the conical inside wall of the fitting typically by engaging the axial end of the ferrule opposite to the nose portion with a nut. The nut has an internal or external thread that is brought into mating engagement with a corresponding thread formed on the fitting, such that rotation of the nut causes axial translation of the ferrule. Consequently, the ferrule at its sealing region is compressed against the conical inside wall of the fitting, and the inside wall defining the internal bore of the ferrule is compressed and swaged against the tube.

In making the fluidic seal, it is easy to apply too much crushing force against the tube, causing the tube to break or otherwise collapse. Particularly when the tube is composed of a material susceptible to cracking such as fused silica, the tip of the ferrule tends to bite into the capillary conduit with excessive force, cracking or breaking it and causing premature failure of a fluidic seal that otherwise seemed to be well-made and leak-free.

In certain gas chromatography applications, it is desirable to ramp the temperature of fittings and other components at fast rates. This requires low thermal mass fittings and ferrules. As ferrules become smaller, it not only becomes difficult to sense when a ferrule is over-compressed, it also increases the difficulty of adding features to prevent over-swaging due to limited machining capabilities. Similarly, for a low thermal mass fitting, the compression nut and threaded portion of the fitting can be eliminated, being replaced by a press fit feature on the ferrule and fitting. While this lowers the thermal mass of the fitting, it also increases the likelihood of over-swaging the ferrule due to the force of the press-fit masking the compression force from the ferrule. Finally, repeated thermal cycling can make the ferrule become loose over time, requiring features to prevent this from occurring.

Therefore, there is a need for providing a ferrule configured to eliminate or at least significantly reduce the tendency to cause sharp crushing of the ferrule tip against the capillary conduit during formation of the fluidic seal.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a ferrule includes: a first end surface; a second end surface spaced from the first end surface along a central axis; a lateral outside surface surrounding the central axis and extending from the first end surface to the second end surface, the lateral outside surface defining an outer radius of the ferrule along a radial direction orthogonal to the central axis; and an inside surface surrounding the central axis and extending from the first end surface to the second end surface, the inside surface defining a bore extending along the central axis and open at the first end surface and the second end surface, wherein: the ferrule comprises a conical section extending from the first end surface toward the second end surface, such that the outer radius increases in a direction away from the first end surface; the lateral outside surface comprises a sealing region at or near the first end surface, the sealing region being configured for forming a sealing interface with a fitting in response to axial compression of the ferrule; and the conical section comprises two or more collapse zones between the sealing region and the second end surface, the collapse zones being axially spaced from each other and from the sealing region, wherein the sealing region and the collapse zones are configured to collapse in sequential order in response to axial compression of the ferrule, starting with the sealing region and followed by each successive collapse zone.

According to another embodiment, a fluidic seal assembly includes: a ferrule according to any of the embodiments disclosed herein; a tube disposed in the bore of the ferrule; and a fluidic fitting comprising an inside fitting wall surrounding the central axis and defining a fitting bore, wherein the ferrule is disposed in the fitting bore and the sealing region is in compressive contact between the inside fitting wall and the tube.

According to another embodiment, a method for forming a fluidic seal includes: inserting a tube in a bore of a ferrule, wherein the ferrule is configured according to any of the embodiments disclosed herein; before or after inserting the tube in the bore of the ferrule, inserting the ferrule in a fitting bore of a fitting, wherein the sealing region of the ferrule contacts an inside fitting wall of the fitting; and axially compressing the ferrule against the inside fitting wall in a direction along the central axis, wherein the sealing region collapses and creates a seal with the inside fitting wall and with the tube; and further axially compressing the ferrule against the inside fitting wall, wherein at least the collapse zone closest to the sealing region axially collapses.

According to another embodiment, a method is provided for designing a ferrule. The ferrule includes a first end, a second end, an outside surface extending from the first end to the second end, and an inside surface defining a bore extending along a central axis from the first end to the second end. The method includes: selecting an axial length and a taper angle for a conical section of the ferrule, the conical section extending from the first end toward the second end; selecting a nose thickness of the ferrule, wherein the nose thickness is defined between the inside surface and a sealing region of the outside surface along a radial direction orthogonal to the central axis, the sealing region being located at or near the first end; selecting a number of annular grooves to form on the outer surface in the conical section, wherein the number is two or greater; selecting a plurality of groove thicknesses of the ferrule at the respective grooves, wherein each groove thickness is defined between the inside surface and the outside surface at the corresponding groove along a radial direction orthogonal to the central axis; forming the conical section such that the conical section has the selected axial length and the selected taper angle, and ferrule has the selected nose thickness; and forming the selected number of grooves in the conical section such that the ferrule has the groove thicknesses selected for the respective grooves.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

As used herein, the term "ferrule" generally encompasses any type of fluidic connector configured for forming a fluidic connection between a tube and a fluidic fitting with which the ferrule engages. The fluidic connection is typically fluid-tight within a specified range of intended operating pressures. In some applications, the ferrule and the tubes to which it may be connected have diameters on the millimeter- or micrometer-scale (e.g., capillary tubes, small-bore chromatographic columns, etc.), in which case the ferrule may be considered as being a microfluidic connector. In some small-scale examples, the ferrule may have a length ranging from 1 to 10 mm, a maximum outer diameter ranging from 1 to 10 mm, and a bore size (inside diameter) ranging from 0.1 to 5 mm. In some examples, the ferrule may have more than one bore running through its length. The ferrule may be configured for joining tubes composed of similar or dissimilar materials (e.g., fused silica glass and metal) and/or different diameters. As one non-limiting example, the ferrule may be utilized in conjunction with analytical instrumentation such as chromatography-based and/or spectrometry-based systems. The ferrule may be designed to operate as a compression fitting. In this case a tube may be inserted into the ferrule's inner bore, or two tubes may be inserted into the opposite ends of the inner bore, and an appropriate technique is then implemented to compress or clamp the ferrule onto the tube(s) to form a fluidic seal, such as by employing a compression nut or other tool.

As used herein, the term "fitting" generally encompasses any type of fluidic component configured for receiving a ferrule and forming a fluidic seal at an outer surface of the ferrule. Forming the fluidic seal establishes a fluid path between the inner bore of the ferrule (or a tube inserted in the ferrule) and the inner bore of the fitting. In some applications, the fitting may be a union configured for forming a sealed joint between two tubes. In some applications, the union may be configured to receive two ferrules and establish a fluid path from the tube in one ferrule to the tube in the other ferrule.

Figure 1A:
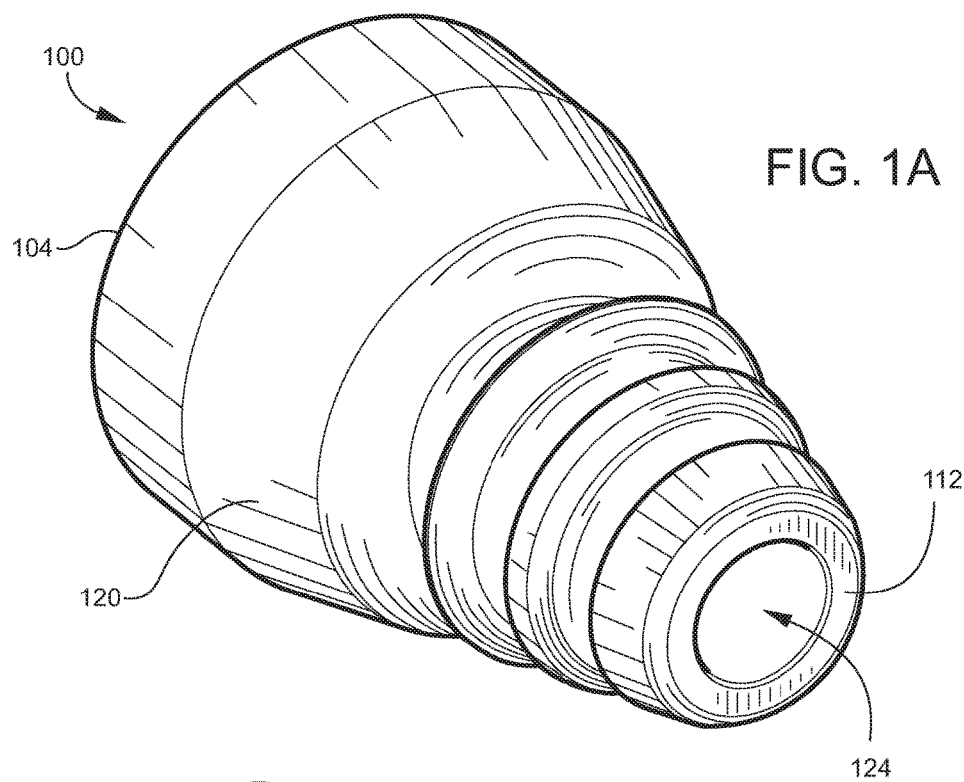
FIG. 1A is a front perspective view of an example of a ferrule according to some embodiments.
Figure 1B:
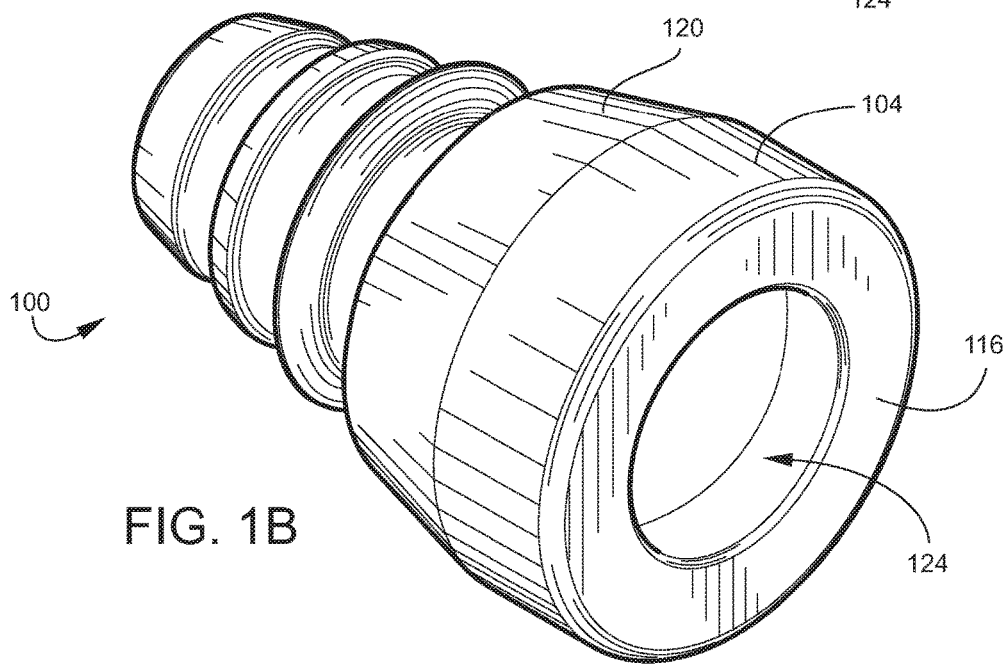
FIG. 1B is a rear perspective view of the ferrule illustrated in FIG. 1A.
Figure 1C:
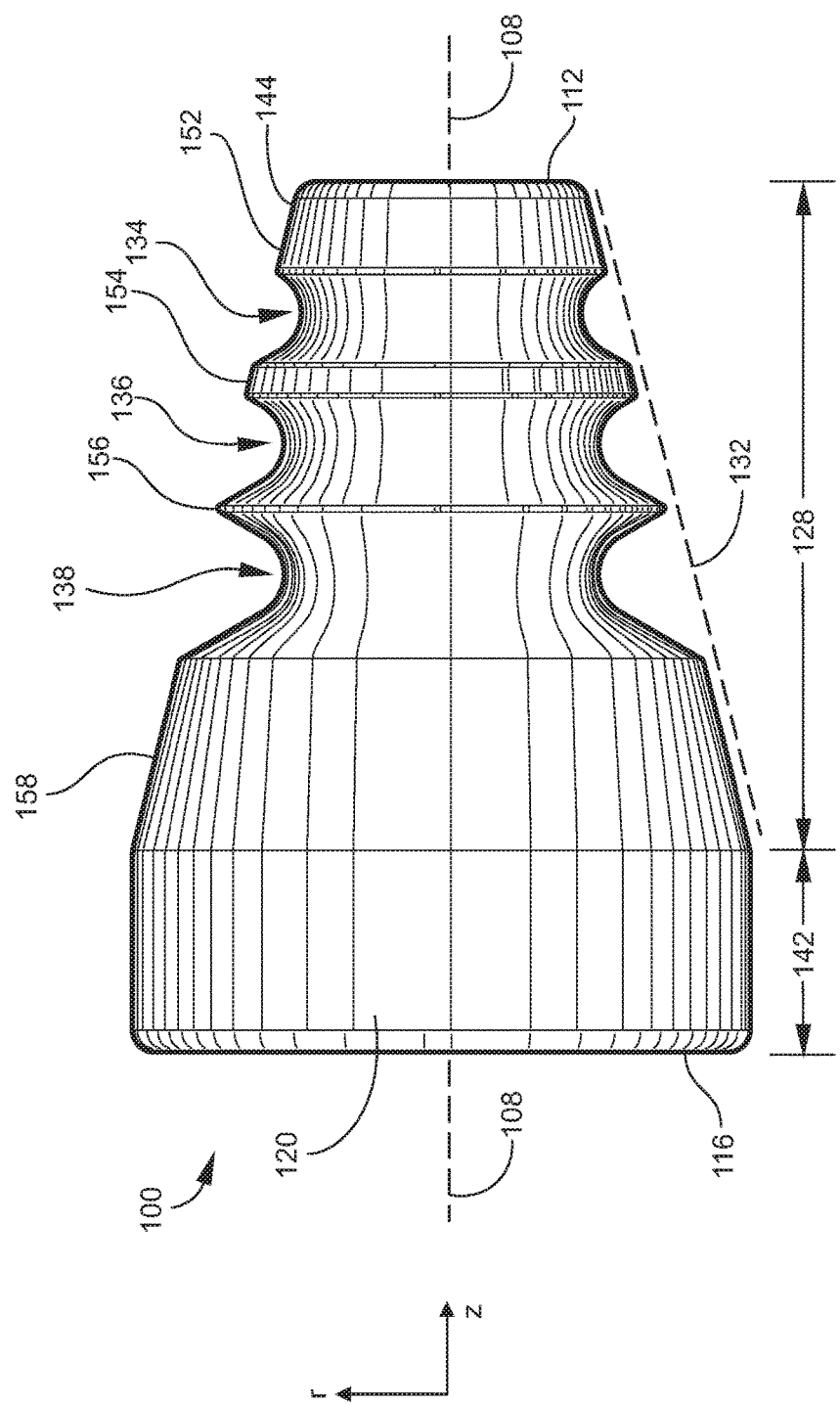
FIG. 1C is a side view of the ferrule illustrated in FIGS. 1A and 1B.
Figure 1D:
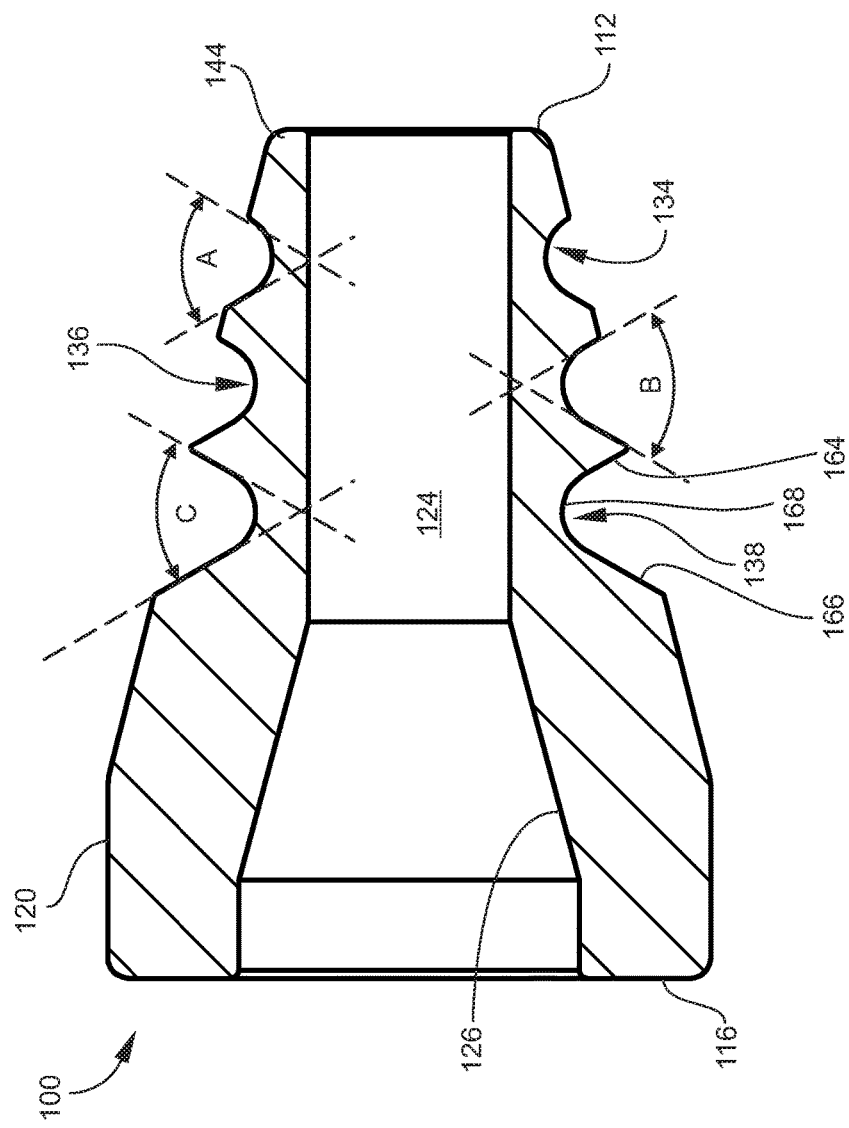
FIG. 1D is a cross-sectional side view of the ferrule illustrated in FIGS. 1A to 1C.
Figure 1E:
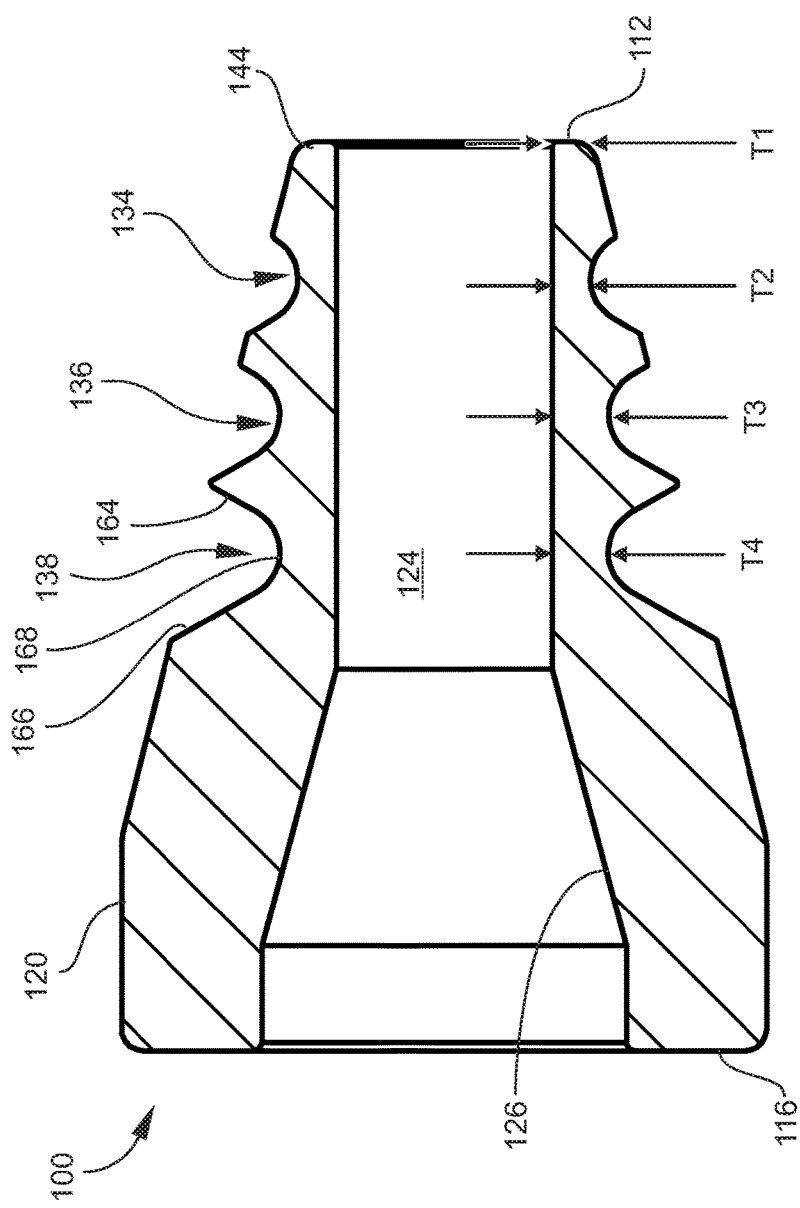
FIG. 1E is another cross-sectional side view of the ferrule illustrated in FIGS. 1A to 1C.

FIG. 1A and FIG. 1B are front and rear perspective views, respectively, of an example of a ferrule 100 according to some embodiments. FIG. 1C is a side view of the ferrule 100, and FIGS. 1D and 1E are cross-sectional side views of the ferrule 100. The ferrule 100 generally includes a ferrule body 104. Typically but not exclusively, the ferrule body 104 has a monolithic (single-piece) construction. As such, the terms "ferrule" and "ferrule body" may be used interchangeably in the present disclosure unless the context dictates otherwise. In a typical embodiment the ferrule body 104 is stainless steel. However, other metals such as aluminum or metal alloys may be utilized. In still other embodiments, the ferrule body 104 may be a polymer composite such as a composite of graphite or glass and one or more polymers (e.g., polyimide, polytetrafluoroethylene (PTFE), etc.).

Typically, the ferrule 100 (ferrule body 104) is axisymmetric about a central axis 108 (FIG. 1C). The ferrule body 104 generally has a length and an outer radius that determines the overall size of the ferrule 100. The length is measured along the central axis 108 from a first (front) end to an axially opposing second (back) end of the ferrule body 104. The front end may also be referred to as the nose or tip of the ferrule 100. The outer radius is measured along a radial direction orthogonal to the central axis 108, and varies along the length of the ferrule body 104 in accordance with the shape of the ferrule body 104. The ferrule body 104 generally includes an outside surface and an inside surface. The outside surface includes a first end surface 112 at the first end, an axially opposing second end surface 116 at the second end, and an outer lateral surface 120 located along the outer radius and extending from the first end surface 112 to the second end surface 116. The inside surface is generally cylindrical and defines an internal bore 124 that extends along the central axis 108 from the first end surface 112 to the second end surface 116, thus providing openings at the first end and second end. As shown in FIGS. 1D and 1E, in some embodiments the internal bore 124 may include one or more conical (tapered) sections 126 providing transitions from larger-diameter sections to smaller-diameter sections, whereby the inside diameter of the opening at the first end may be different (e.g., smaller) than the inside diameter of the opening at the second end to facilitate inserting the tubing to be joined into the ferrule 100.

As illustrated, the ferrule 100 includes a conical (tapered) section 128 (FIG. 1C). Along the length of the conical section 128, the outer radius of the ferrule body 104 progressively reduces in the direction toward the first end. The conical section 128 occupies a conical, outer envelope or profile partially depicted by a dashed line 132 in FIG. 1C. The angle of the outer envelope 132 relative to the central axis 108 (the cone angle, or taper angle, of the conical section 128) may or may not be constant over the entire length of the conical section 128. In some embodiments and as illustrated, the progressive reduction in outer radius corresponding to the outer envelope 132 is interrupted by two or more annular grooves 134, 136, and 138, described below. The conical section 128 begins at the first end and continues in the direction of the second end over at least a portion of the length of the ferrule 100. In some embodiments and as illustrated, the conical section 128 may transition to (adjoin) a straight section 142 of the ferrule 100 that continues to the second end. In some embodiments, this straight section 142 may be sized to form a press-fit connection with a fitting while the ferrule 100 is in use. In other embodiments, the conical section 128 may extend over the entire length of the ferrule 100. A portion of the conical section 128 at the front end defines a sealing region 144 (FIG. 1C). The sealing region 144 corresponds to the portion of the outer lateral surface 120 of the ferrule 100 that makes contact with the conical inside wall of a fluid fitting, i.e., the region where a fluidic seal is formed between the ferrule 100 and the fluid fitting.

In some embodiments, the ferrule 100 includes two or more grooved regions in the conical section 128. The grooved regions include respective annular grooves 134, 136, and 138 that are part of the outer lateral surface 120. In the embodiment specifically illustrated, the ferrule 100 includes a first groove 134, a second groove 136, and a third groove 138, while in other embodiments may include more or less than three grooves. Portions of the outer lateral surface 120 adjacent to the annular grooves 134, 136, and 138 and in the conical section 128 may be referred to as bands. In the illustrated embodiment, the ferrule 100 includes a first band 152 between the first end and the first groove 134, a second band 154 between the first groove 134 and the second groove 136, a third band 156 between the second groove 136 and the third groove 138, and a fourth band 158 after the third groove 138. The annular grooves 134, 136, and 138 and bands 152, 154, 156, and 158 collectively make up the portion of outer lateral surface 120 that is located in the conical section 128. The outer radius of one or more of the bands 152, 154, and 156 may define the outer radius of the outer envelope 132 occupied by the conical section 128. The sealing region 144 may correspond to all or a part of the first band 152. In some embodiments, the widths of the bands 152, 154, and 156 are successively smaller in the direction of the second end, at least until the last annular groove is encountered. In the illustrated embodiment, for example, the second band 154 is smaller than the first band 152 and the third band 156 is smaller than the second band 154.

The shapes of the annular grooves 134, 136, and 138 may be characterized by the shape or curvature of their profiles. In the present context, the profile of a given groove is taken to be the profile observed from the perspective of a side view of the ferrule 100, for example, as shown in FIGS. 1C, 1D, and 1E. Each groove profile thus lies in a transverse plane or r-z plane of the ferrule 100, where z is a coordinate of the central axis 108 and r is a coordinate of the radial axis orthogonal to the central axis 108 (FIG. 1C) of the ferrule 100. Hence, each groove profile may be defined by a curve containing points definable by (r, z) coordinates. The bottom (innermost) sections, or roots, of the annular grooves 134, 136, and 138 (in the vicinity of the minimum radius of the annular grooves 134, 136, and 138) may be generally round and relatively blunt as illustrated, or may be relatively sharper than those illustrated, which may be limited by the capabilities of the fabricating technique employed. Each groove profile may also be considered as being concave and opening up generally in a radially outward direction away from the central axis 108.

Referring to FIG. 1D, the profile or curvature of each annular groove 134, 136, and 138 is generally made up of three main components: a first (front) groove section or flank 164 angled or leaning toward the first (front) end of the ferrule 100, a second (back) groove section or flank 166 angled or leaning toward the second (back) end of the ferrule 100, and a bottom groove section or root 168. The bottom groove section 168 is between, and adjoins, the first groove section 164 and the second groove section 166, and includes the minimum radius of the annular groove 134, 136, or 138. Pairs of intersecting dashed lines in FIG. 1D generally correspond to the first groove section 164 and second groove section 166 of each annular groove 134, 136, and 138. Depending on the curvature of a given groove, the dashed lines may lie directly on all or a majority of the first groove section 164 and second groove section 166, or may be tangential to respective points on the first groove section 164 and second groove section 166. Each annular groove 134, 136, and 138 has a groove angle, which is the angle at which the annular groove 134, 136, and 138 (or the groove profile) diverges outward from the central axis 108 as seen in a side profile, or the angle between the first groove section 164 and the second groove section 166. In FIG. 1D, the groove angle is the angle between the pair of dashed lines associated with each annular groove 134, 136, and 138. Hence, the first groove 134 has a first groove angle A, the second groove 136 has a second groove angle B, and the third groove 138 has a third groove angle C. In the illustrated embodiment, the groove angles A, B, and C are equal, specifically 60 degrees in the illustrated example. In other embodiments, one or more groove angles may be different than the other groove angles. In some embodiments, the groove angles may be in a range from 30 to 90 degrees.

It will be understood that the groove profiles and groove angles A, B, and C shown in FIG. 1D are initial or nominal profiles and angles, i.e., before the ferrule 100 has been swaged or installed in a fluidic fitting. In use, axial compression of the ferrule 100 applied in the course of forming a fluidic seal may alter one or more of the groove profiles and groove angles in a manner described below.

The geometry or structure of the ferrule 100 (ferrule body 104) is configured (shaped and sized) to include axially collapsible zones, also referred to herein as axial collapse zones or simply collapse zones. Generally, there is a collapse zone associated with the nose (tip) or the ferrule 100 (i.e., the sealing region 144) and with one or more other geometric or structural features of the ferrule 100. In the illustrated embodiment, collapse zones are implemented by, in addition to the sealing region 144, a plurality of grooved regions respectively located at successive greater axial distances from the first end of the ferrule 100. In the present "three-groove" embodiment, the grooved regions may be considered as corresponding to the annular grooves 134, 136, and 138 along with the solid portions of the ferrule 100 between the annular grooves 134, 136, and 138 and the internal bore 124. Accordingly, the present embodiment provides four distinct collapse zones: a first collapse zone associated with the sealing region 144, a second collapse zone associated with the first annular groove 134, a third collapse zone associated with the second annular groove 136, and a fourth collapse zone associated with the third annular groove 138. Other embodiments may provide more or less than four collapse zones. Each collapse zone has an associated thickness, i.e., the thickness in the radial direction of the solid material of the ferrule 100 between the inside and outside surfaces thereof. Referring to FIG. 1E, the respective thicknesses of the collapse zones are generally indicated at T1, T2, T3, and T4. The thickness T1 between the inside surface and the sealing region 144 is also referred to herein as the nose thickness. The thicknesses T2, T3, and T4 between the inside surface and the respective grooves 134, 136, and 138 are also referred to herein as groove thicknesses.

The thicknesses T1, T2, T3, and T4 of the collapse zones are configured to allow successive (sequential in time and spatially) axial collapse of the collapse zones (beginning with the first collapse zone at the sealing region 144, followed by the second collapse zone at the first annular groove 134, and so on) as the ferrule 100 is compressed against a fluidic fitting during installation of the ferrule 100 in the fitting to form a fluidic seal. "Axial" collapse refers to deformation of a region of the ferrule 100 generally in an axial direction, i.e., in a direction generally oriented along the central axis 108. The thickness of each collapse zone may be different from the thicknesses of the other collapse zones. For example, in the illustrated embodiment the thicknesses T1, T2, T3, and T4 of the collapse zones successively increase in the direction away from the sealing region 144. Thus, T1<T2<T3<T4. In some embodiments, each collapse zone thickness is 10% to 50% greater than the preceding collapse zone thickness, for example T2 is 10% to 50% greater than T1, T3 is 10% to 50% greater than T2, and so on.

Figure 2A:
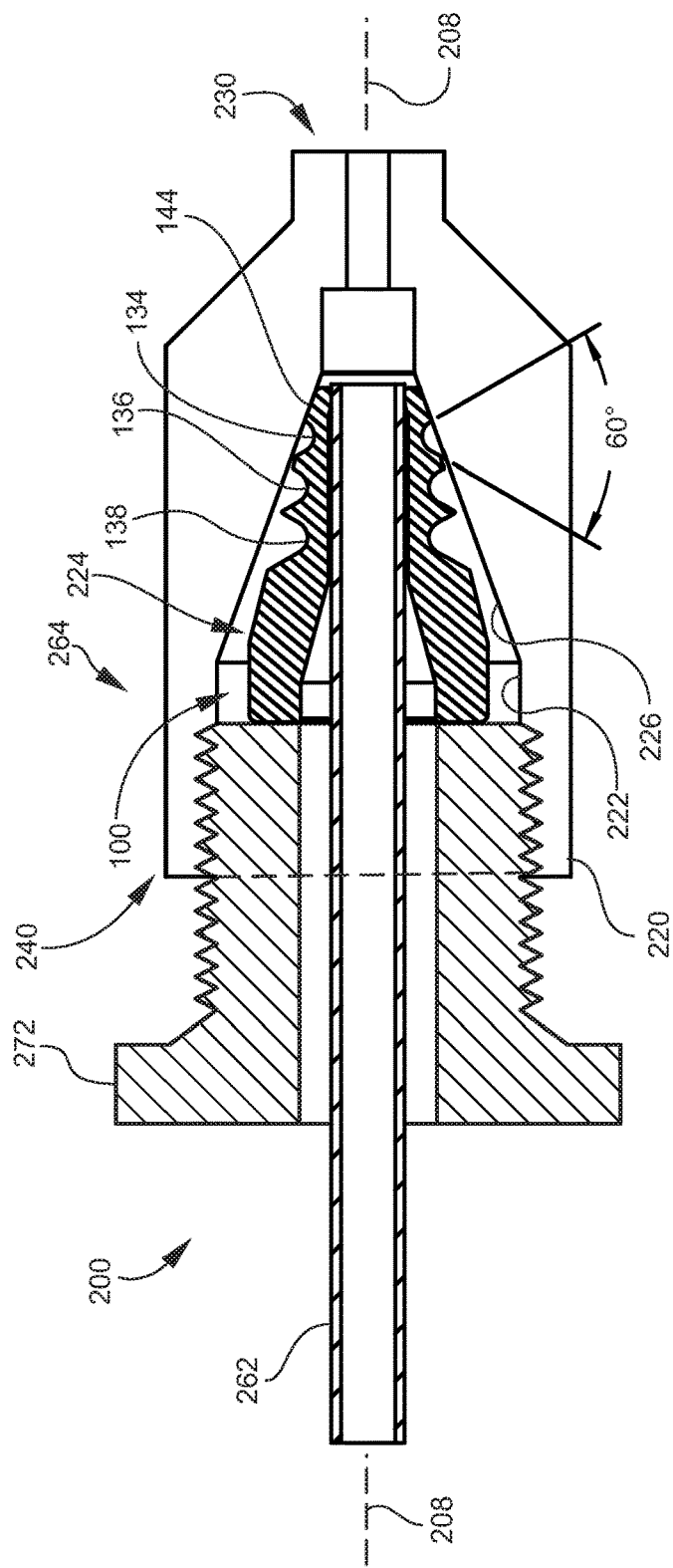
FIG. 2A is a cross-sectional side view of an example of a fluidic seal assembly in which a ferrule, such as illustrated in FIGS. 1A to 1E, and a tube have been inserted into a fluidic fitting and the ferrule is in an un-swaged or pre-swaged state, according to some embodiments.
Figure 2B:
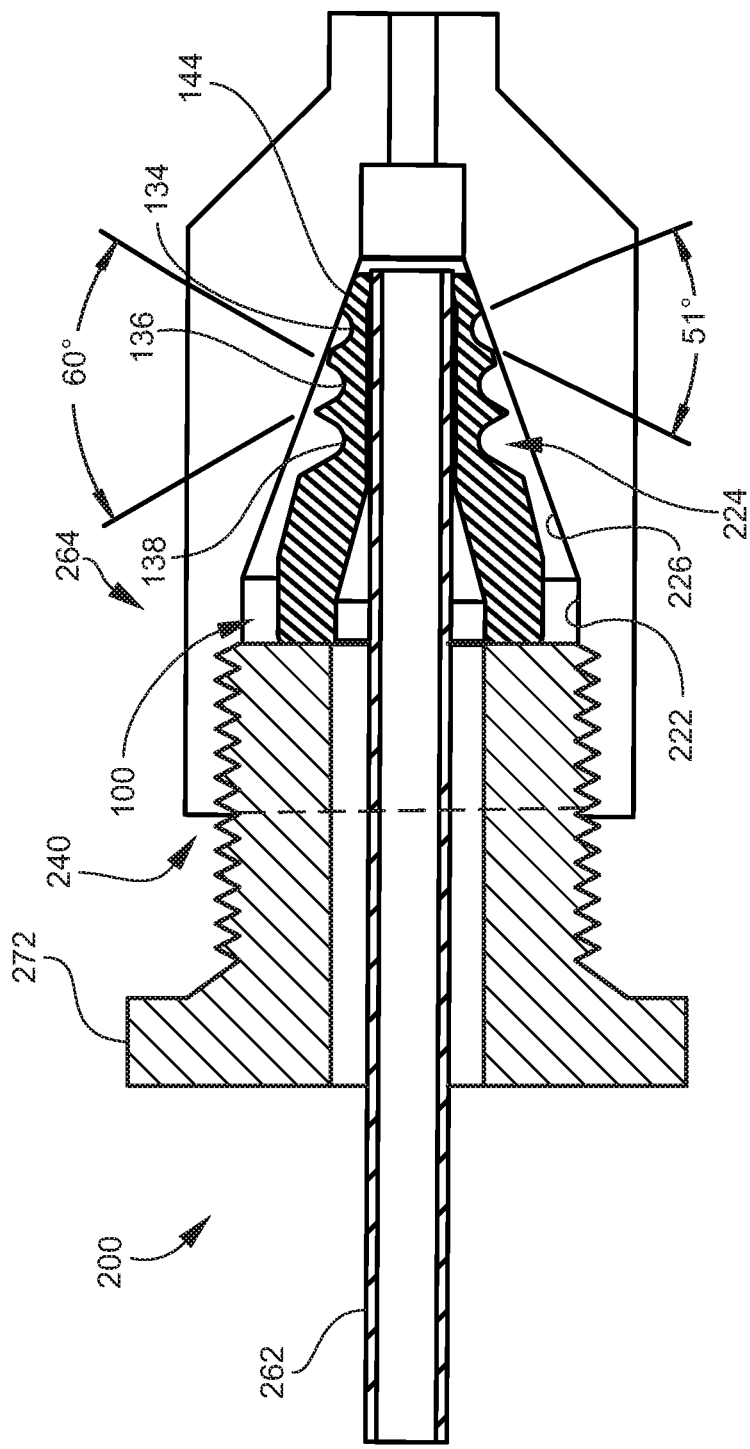
FIG. 2B is a cross-sectional side view of the fluidic seal assembly illustrated in FIG. 2A after compression of the ferrule against the fluidic fitting and the tube.
Figure 2C:
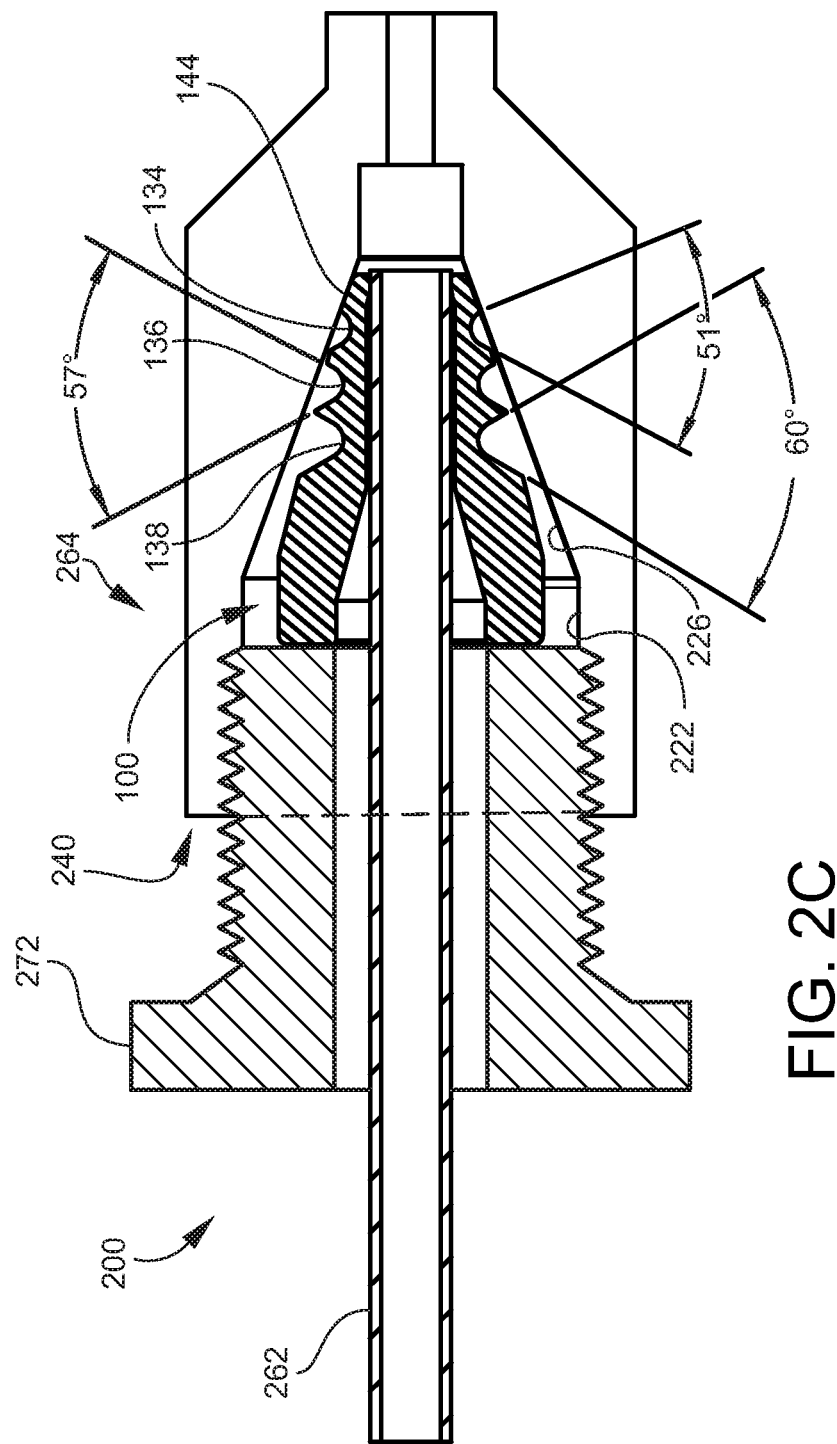
FIG. 2C is a cross-sectional side view of the fluidic seal assembly illustrated in FIGS. 2A and 2B after further compression of the ferrule against the fluidic fitting and the tube.

FIGS. 2A to 2C sequentially illustrate an example of a method for forming a fluidic seal assembly (or ferrule/fitting system) 200 according to some embodiments, utilizing a ferrule according to the present disclosure such as the ferrule 100 described above and illustrated in FIGS. 1A to 1E. Generally, the fluidic seal assembly 200 is created by forming a fluidic seal between the ferrule 100 and a tube 262 and between the ferrule 100 and a fluidic fitting 264 of appropriate configuration.

FIG. 2A is a cross-sectional side view of an example of the fluidic seal assembly 200 according to some embodiments. The fluidic seal assembly 200 includes the ferrule 100, the tube 262, and the fluidic fitting 264. The tube 262 may be constructed of fused silica or other suitable material such as various metals and polymers. In some embodiments the tube 262 is of a capillary-scale or microfluidic-scale size. The fluidic fitting 264 may generally include a fitting body. The fitting body includes an outside fitting surface 220 and an inside fitting wall 222 surrounding a central axis 208. The inside fitting wall 222 defines an internal fitting bore 224 that extends along the central axis 208 from a first (front) fitting opening 230 to a second (back) fitting opening 240. The inside fitting wall 222 typically includes at least one conical (tapered) section 226 for forming a sealing interface with the sealing region 144 of the ferrule 100, and may include more than one conical section. In some embodiments, the sealing region 144 of the ferrule 100 has a taper angle (cone angle) in a range from 20 to 90 degrees, and the conical section 226 of the fitting 264 has a taper angle (cone angle) in a range from 30 to 120 degrees. The taper angles are included angles about the central axis 208, i.e., the taper angles are measured relative to the central axis 208. The inside fitting wall 222 may also include one or more stepped transitions. In all such cases, the first fitting opening 230 and the second fitting opening 240 may have different inside diameters.

FIG. 2A illustrates an initial stage of forming the fluidic seal, in which the tube 262 is inserted in the internal bore of the ferrule 100 and the ferrule 100 and tube 262 are inserted into the internal fitting bore 224 of the fluidic fitting 264 via the second fitting opening 240. Alternatively, the ferrule 100 may first be inserted into the internal fitting bore 224, and the tube 262 then inserted into the internal fitting bore 224 and into the internal bore of the ferrule 100. The ferrule 100 is inserted through the fitting bore 224 until its sealing region 144 makes contact with a corresponding sealing region of the inside fitting wall 222 of the conical section 226. FIG. 2A depicts the ferrule 100 while still in an un-swaged state. At this stage, the groove angles of the annular grooves 134, 136, and 138 are at their initial values. In the present example, the initial groove angles are the same and are each 60 degrees. Alternatively, the ferrule 100 may be pre-swaged to the tube 262 before being inserted into the internal fitting bore 224, in which case the groove angles may no longer be at their initial values.

FIG. 2B is a cross-sectional side view of the fluidic seal assembly 200 after compressing the ferrule 100 against the inside fitting wall 222 of the fluidic fitting 264, which also compresses the ferrule 100 against the tube 262. Compression may be achieved by axially translating the ferrule 100 along the central axis 208, which may be done by any suitable means such as with the use of a threaded nut or a tool as appreciated by persons skilled in the art. The nut may hold the ferrule 100 in place after it is swaged or may thereafter be removed if a press fit is formed between the back diameter of the ferrule 100 and the inside back diameter of the fitting 264. Due to the axial compression, the sealing region 144 will bottom out and proceed to be coined against the corresponding sealing region of the inside fitting wall 222, and the ferrule 100 will be swaged against the tube 262. The ferrule 100 is configured such that the primary movement of the ferrule 100 against the tube 262 occurs at the nose of the ferrule 100, where the fluidic seal will form against the inside fitting wall 222 and also against the tube 262. When applied with a proper amount of force, axial compression of the ferrule 100 forms a fluid-tight sealing interface between the ferrule 100 and the inside fitting wall 222 at their respective sealing regions, and a fluid-tight sealing interface between the ferrule 100 and the outer surface of the tube 262, without damage to or breakage of the tube 262.

Conventionally at this stage, subsequent axial compression will tend to over-compress the sealing region 144, consequently damaging the tube 262 and breaking the tube 262 if constructed of a material such as fused silica. In embodiments of the presently disclosed ferrule 100, however, the additional collapse zones provided behind the sealing region 144 (corresponding to the annular grooves 134, 136, and 138) are configured to allow the ferrule 100 to axially collapse in a predictable, predetermined, and controlled fashion, thereby protecting against over-compression of the sealing region 144 (i.e., the first collapse zone). The ferrule 100 is configured to have staged collapse zones that provide successively stronger resistance to axial collapse due at least in part to their successively increased thicknesses T1, T2, T3, and T4 (FIG. 1E). By this configuration, an initial amount of axial compression will collapse the ferrule 100 at the sealing region 144 (first collapse zone) enough to form a reliable, effective sealing interface between the sealing region 144 and the inside fitting wall 222, and between the inside surface of the ferrule 100 and the outside surface of the tube 262.

The grooved regions (additional collapse zones) are configured to protect the sealing region 144 (first collapse zone) from over-compression by preferentially (and sequentially) collapsing before any further collapse of the sealing region 144 might occur due to over-compression. Thus, additional axial compression will cause the first groove 134 (second collapse zone) to collapse, thereby avoiding further collapse of the sealing region 144 (first collapse zone). Further axial compression will subsequently cause the second groove 136 (third collapse zone) to collapse, again avoiding further collapse of the sealing region 144 (first collapse zone). Still further axial compression will subsequently cause the third groove 138 (fourth collapse zone) to collapse, again avoiding further collapse of the sealing region 144 (first collapse zone), and so on depending on how many grooved regions are provided. As each collapse zone collapses, the ferrule material will work-harden in the grooved regions and there will be less and less ability to collapse the previously collapsed zones. It can be seen that the grooved regions and associated staged collapse zones spread out the deformations caused by axial compression over a broader region of the compressed ferrule 100 as compared to a situation in which the grooved regions were absent. The grooved regions impart a tolerance to axial compression of the ferrule 100 that compensates for any over-compression that might occur, thereby mitigating the swaging or crushing of the ferrule 100 against the tube 262 and preventing damage or breakage of the tube 262. The response of the grooved regions to applied compression may be characterized as a staged or progressive "accordion effect."

Further reference is made to FIG. 2C, which is a cross-sectional side view of the fluidic seal assembly 200 after further compression of the ferrule 100 beyond what is shown in FIG. 2B.

The response of the grooved regions to applied axial compression of the ferrule 100 may be visualized by comparing the groove angles in FIGS. 2A, 2B, and 2C. In FIG. 2A the initial groove angles are, as one non-limiting example, each 60 degrees as noted above. In FIG. 2B, after compression, the groove angle of the first groove 134 has been reduced to 51 degrees due to deformation in the associated second collapse zone, while at this stage the groove angles of the second groove 136 and the third groove 138 remain at or about 60 degrees. In FIG. 2C, after further compression, the groove angle of the second groove 136 has been reduced to 57 degrees due to deformation in the associated third collapse zone, while at this stage the groove angle of the third groove 138 remains at or about 60 degrees. At the stage depicted in FIG. 2C, the groove angle of the first groove 134 may remain at or about the reduced value of 51 degrees due to work-hardening in the region of the first groove 134 and transferring of the compressive forces to the second groove 136.

Figure 2D:
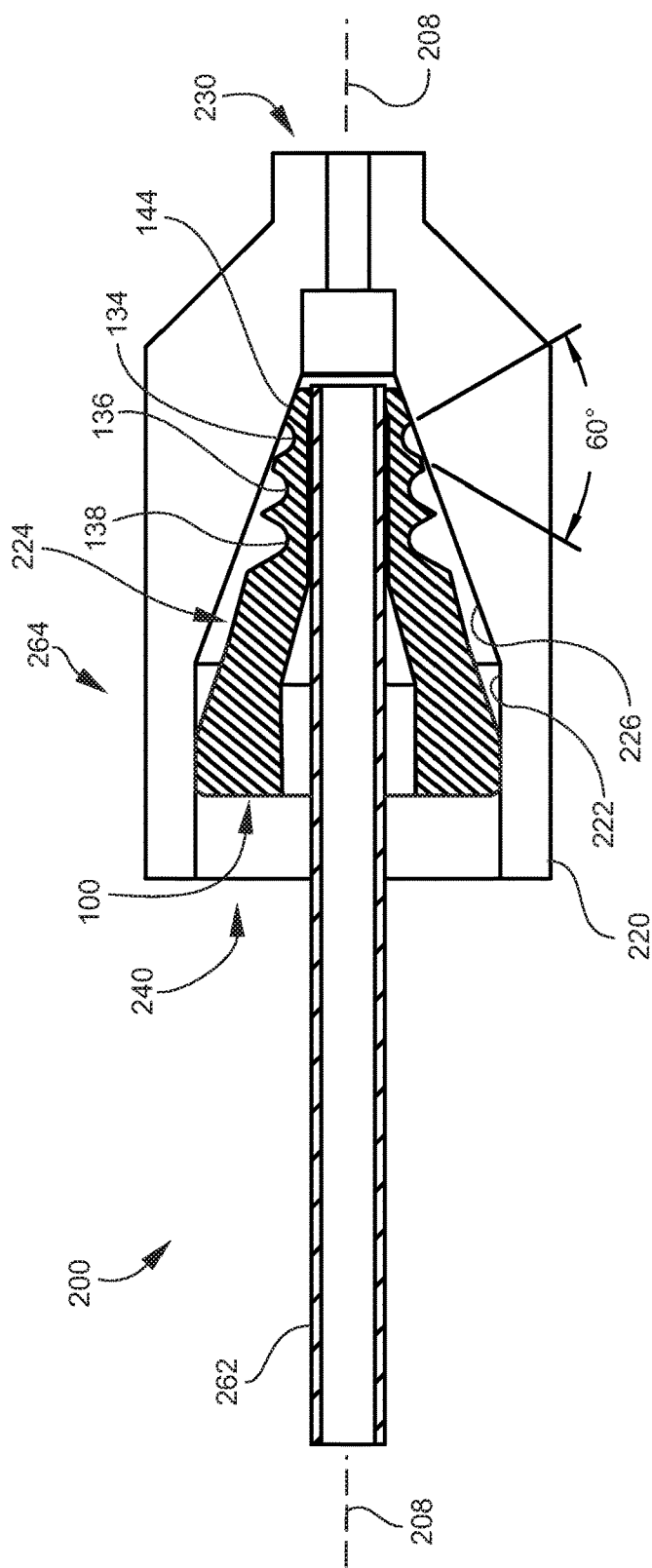
FIG. 2D is a cross-sectional side view of another example of a fluidic seal assembly similar to FIG. 2A, but with a ferrule being retained by press-fit instead of a backing nut.

As appreciated by persons skilled in the art, once formation of the fluidic seal is complete, the ferrule 100 may be retained in place by any suitable means such as, for example, a backing nut 272. Alternatively, as shown in FIG. 2D the ferrule 100 may be configured (i.e., sized and shaped) such that its rear section is press-fitted against (i.e., makes an interference fit with) the inside fitting wall 222. Other means for retaining the ferrule 100 may be employed, such as a press-fitted retainer, integrated catch features, etc.

In a further example of a method for forming a fluidic seal, a tube is inserted in a bore of a ferrule as disclosed herein (e.g., the ferrule 100 described above and illustrated in FIGS. 1A to 2C). Before or after inserting the tube in the bore of the ferrule, the ferrule is inserted in a bore of a fitting such that a sealing region of the ferrule (located on the outside surface of the ferrule at or near its front end) contacts an inside fitting wall of the fitting. The ferrule is then axially compressed against the inside fitting wall, i.e., is compressed in a direction along the central axis. Due to the axial compression, the ferrule material at the sealing region collapses and creates a seal with the inside fitting wall and with the tube. Specifically, a seal is created between the sealing surface and the inside fitting wall, and a seal is created between the inside surface of the ferrule (that defines the internal ferrule bore) and the outside surface of the tube. As described above the ferrule is configured to include, in addition to the collapse zone provided by the sealing region, two or more collapse zones axially spaced from each other and from the sealing region. The sealing region and the collapse zones are configured to collapse in sequential order in response to axial compression of the ferrule, starting with the sealing region and followed by each successive collapse zone. Thus, after the ferrule makes initial contact with the inside fitting wall and is axially compressed to form the fluid seal, further axial compression of the ferrule against the inside fitting wall (e.g., over-compression) causes at least the collapse zone closest to the sealing region to axially collapse, which may be followed by the successive collapsing of one or more other collapse zones provided. In a preferred embodiment, collapsing of the collapse zones provided in addition to the sealing region is preferential to further collapsing of the sealing region. In other words, if enough force is applied to cause the collapse zone closest to the sealing region to collapse, the collapsing of that collapse zone will occur without any further appreciable collapsing of the sealing region. The ferrule may be configured such that the collapse zones provided after the sealing region will collapse only in the event of over-compression. That is, if an ideal amount of sealing force is applied, the ferrule can form effective ferrule-fitting and ferrule-tube sealing interfaces without the occurrence of collapsing after the sealing region. If, however, excessive force is applied, the additional collapse zones are effective to protect against over-compression at the sealing region in the manner described herein.

Examples of some considerations that may be given for designing and fabricating a ferrule effective to protect against over-compression, such as the ferrule 100 described above will now be described. Generally, the ferrule 100 is designed based on the constraints of the ferrule/fitting system. The constraints include the size (inside diameter and length) of the fitting (e.g., the fitting 264 shown in FIG. 2A) and the outside diameter of the tube or column (e.g., the tube 262 shown in FIG. 2A) being joined by the ferrule/fitting system. The overall size of the fitting 264 is driven by the size of the tube 262, as well as the fluidic and thermal performance requirements of the system and by the method of assembly and other user handling. For example, a joint requiring high rates of change in temperature mandates a small mass and good exposure to the heat sinking body or medium. As small delicate parts, such as a fused silica capillary, are being joined in applications where high rates of temperature change are necessary, the size of the ferrule/fitting system moves towards the limits of machinability of small features. A tube 262 such as a fused silica capillary may have an internal diameter in a range from about 50 µm to about 500 µm and a wall thickness in a range from about 50 µm to 80 µm, resulting in outer diameters of 150 µm to 620 µm. On the other hand, larger fitting systems are suitable for isothermal settings where more user access and serviceability are desired.

As described above, a ferrule-based fitting creates two fluid-tight seals. The first seal is between the inside of the ferrule nose (tip) and the outside of the tube 262. The second seal is between the outside of the ferrule nose (the sealing region 144) and the portion of the conical section 226 of the fitting 264 that contacts the sealing region 144 (see, e.g., FIG. 2A). These seals are formed when the ferrule 100 is pushed in axial translation, it bottoms on the conical section 226 of the fitting 264, and its nose is plastically deformed. The taper angle of the conical section of the ferrule 100 (at least at the sealing region 144), also termed the ferrule front angle, and the corresponding taper angle of the conical section 226 of the fitting 264 (particularly the portion that contacts the sealing region 144), also termed the fitting angle, are chosen so as to ensure the effectiveness and integrity of the two fluid-tight seals. The ferrule front angle and the fitting angle may also be chosen so as to control the location of the two fluid-tight seals. As noted above, in some embodiments the ferrule front angle may be in a range from 20 to 90 degrees, and the fitting angle may be in a range from 30 to 120 degrees. Preferably, the fitting angle is larger than the ferrule front angle so that contact between the ferrule 100 and the fitting 264 occurs only at the front sealing region 144. A smaller ferrule front angle and a smaller fitting angle provide a more efficient squeeze on the ferrule nose to form the seal, and the increased axial translation from a smaller ferrule front angle provides more feedback on its movement. However, a ferrule with a small front angle can be easier to become wedged or stuck inside the fitting bore, because a larger normal swaging force generates a larger friction force. In choosing the ferrule front angle, the materials to be used and the application are also considered. Metal ferrules, having high strengths and smaller friction coefficients, are suitable to have small front angles. In some embodiments, the ferrule surfaces are coated with lubricant such as gold or silver to reduce friction coefficient of the ferrule. On the other hand, ferrules made with graphite or a composite of graphite and polymer are more prone to becoming wedged or stuck, such that larger taper angles may be preferred when utilizing such materials. Replaceable/reusable ferrules will commonly use a larger front angle to minimize the problem of wedging or sticking. Other means to loosen a wedged or stuck ferrule are available if the taper angle cannot be large in a particular application.

Selection of the thickness of the ferrule 100 at its nose (thickness T1 shown in FIG. 1E) may be based on the inside diameter (ID) of the fitting 264, the outside diameter (OD) of the tube 262, the ferrule front angle, and the ferrule material. For a metal ferrule, the thickness T1 may be relatively small because the strength of the metal allows efficient plastic deformation, which provides the colleting function of the ferrule. By comparison, a softer material such as graphite-polyimide (e.g., VESPEL® material) will need to be thicker to spread the deformation over a broader face and thereby allow the compression of the material in a stable way around the tube 262, as comparatively thinner material may relax and loosen the compression seal. Thus, a larger ferrule nose diameter may be a consequence of the thicker material required in a part made out of weak, soft, and/or porous materials (e.g., graphite/graphite-VESPEL® material).

A ferrule fabricated in accordance with the above design considerations may be effective for forming fluid-tight seals in various applications. However, this effectiveness may assume a perfect or near perfect amount of force is applied to create the seal, such that the seal is created without compromising the reliability or integrity of the seal and without damaging the tube 262. That is, the above design considerations alone may not be sufficient for protecting against the deleterious effects of over-compression, which in practice often occurs as noted above. As described herein, multiple collapse zones may be integrated into the design of the ferrule 100 to compensate for excessive force being applied to the ferrule 100. As described herein, the collapse zones may be realized by providing annular grooves (e.g., grooves 134, 136, and 138 shown in FIGS. 1E and 2A) at respective axial locations on the outside surface of the ferrule 100, and at which the ferrule body has respective thicknesses (e.g., thicknesses T2, T3, and T4 shown in FIG. 1E).

The design of the ferrule 100 may entail determining the angle(s) of the grooves (e.g., groove angles A, B, and C shown in FIG. 1D), the axial positions of the grooves (e.g., the spacing between the grooves and their distances from the front end or sealing region 144 of the ferrule 100), and the number of grooves provided. As noted above, in some embodiments the groove angle may be in a range from 30 to 90 degrees. The range of possible groove angles is generally constrained by the capability of the cutting tools available for use in forming the grooves. The choice of groove angle may be based, at least preliminarily, on the angle made by a readily available cutting tool, which can reduce the manufacturing cost of the ferrule 100. For example, a cutting tool of 60 degrees is common and thus the groove angle selected may be 60 degrees. However, for a fixed available space that is dictated by the size of the fitting 264, the number of grooves that can be fit in that space depends on the size of the groove angle. Accordingly, a large groove angle limits the number of grooves that can be provided. Thus, the determination of the number of grooves to include in the ferrule configuration may begin with selecting a preliminary groove angle (e.g., 60 degrees), and then increasing or decreasing the groove angle as necessary, which may be based on groove thickness (e.g., T2, T3, T4, etc.) and the spacing between adjacent grooves needed to be able to fit a minimum number of grooves (e.g., at least two grooves) in the ferrule 100.

Moreover, like the groove angle, in practice the range of possible groove root radii is generally constrained by the capability of available cutting tools. The size of the groove root radius may also be chosen to minimize the functionality drift caused by cutting tool wear. In the present context, the groove root radius corresponds to the radius of a circle tangent to the innermost point of a groove (e.g., the root 168 shown in FIG. 1E), and determines the degree of bluntness or sharpness of the groove. As one non-limiting example, the groove root radius may be in a range from 0.1 mm to 0.5 mm.

Designing the grooves to serve as collapse features may also involve maximizing the collapsibility of the ferrule body (i.e., the remaining ferrule body beyond the ferrule nose at which the front sealing region 144 is located) without compromising the internal ferrule bore. Stated differently, another design consideration may relate to configuring the ferrule 100 such that over-compression will collapse more than just the nose of the ferrule 100. Given the size of the ferrule 100 and the taper angles of the ferrule 100 and the fitting 264, a set of grooves may be configured so as to provide predictable staged compression/collapsing. During axial compression of the ferrule 100, the ferrule nose is subjected to a normal force given by the angle of the ferrule 100 with respect to the fitting body and which directly forms the ferrule-fitting/ferrule-tube seal. This normal force is highly concentrated where formation of the seal is desired, i.e., at the nose. The seal forms as the normal force deforms the ferrule material. The seal between the ferrule 100 and the tube 262 forms as the result of the ferrule nose being swaged against the tube 262. The axial length along which the ferrule 100 contacts and compresses against the tube 262 may be referred to as the nose seal deformation zone. In some embodiments, the axial distance along which the nose seal deformation zone extends is at least about 20% of the inside diameter of the ferrule 100 (or outside diameter of the tube 262). The ferrule-tube contact interface, in addition to forming a fluid-tight seal, stabilizes the ferrule/tube seal against side-to-side motion and against axial forces. Setting the axial length of the nose seal deformation zone to at least about 20% may facilitate the stabilizing functions of the ferrule-tube contact interface. The deformation leading to formation of the seal changes the properties of the ferrule material, hardening and strengthening the strained volume along this length. This increased strength has two effects: First, it becomes more and more difficult to deform the hardened/strengthened material; and second, the deformation is more likely to crush the tube 262 because of the proximity to the tube 262 and lack of sufficient ductility.

Crushing of the tube 262 may be prevented by providing staged compression/collapsing, thereby promoting collapsing or buckling at the grooves instead of at the nose or on the inner wall of the ferrule 100. To provide staged compression/collapsing, the thickness T2 (and thus strength) of the ferrule body at the first groove 134 closest to the sealing region 144 (FIG. 1E) may be made to be greater than the original thickness T1 (and thus strength) of the sealing region 144 before compression. Similarly, the thicknesses of additional grooves provided (e.g., T3, T4, and so on) may be progressively greater than the preceding grooves. In some embodiments, the thickness T2 of the ferrule body at the first groove 134 is 10% to 50% greater (and thus stronger) than the original thickness T1 of the sealing region 144 before compression. Also, the axial distance (spacing) of the first groove 134 (e.g., the point at which the first flank of the first groove 134 begins) from the sealing region 144 (e.g., from the point at which the sealing region 144 ends) may be set so as to achieve independence of the collapse features and thereby ensure staged compression/collapsing at distinct collapse zones. As noted above the ferrule-tube contact interface, in addition to forming a fluid-tight seal, stabilizes the ferrule/tube seal against side-to-side motion and against axial forces. Thus, the axial distance between the sealing region 144 and the first groove 134 should be great enough such that the presence of the first groove 134 does not interfere with the stabilizing functions of the ferrule-tube contact interface. Also, as described earlier, the groove angle and root radius are selected in view of available tool technology and so as to fit a desired number of grooves within the space available on the conical section of the ferrule 100.

Similarly, the thickness T3 of the ferrule body at the second groove 136 (FIG. 1E) may be made 10% to 50% greater (i.e., stronger) than the original thickness T2 of the first groove 134. Also, the collapse zone associated with the second groove 136 should be independent from the previous collapse zone(s) and provide predictable buckling. Thus, in some embodiments the axial spacing between the first groove 134 and the second groove 136 is large enough that the grooves 134 and 136 do not overlap, thereby assuring that the collapse zones are independent. As necessary, the tops of the grooves may overlap slightly so long as the straining region near the root of one groove does not overlap with the straining region of the other groove. The groove spacing depends on the taper angle of the ferrule 100. The practical aspects of adding the grooves may tend to pack the entire set of grooves toward the nose of the ferrule 100 given the design considerations described above. Nonetheless, the grooves may be separated by greater distances provided sufficient space is available in a given application.

The number of grooves depends primarily on the space available. The more grooves, the more collapsing the ferrule 100 can provide, and the less over-swaging that will occur. However, more grooves cost more in manufacturing. In applications in which the ferrule 100 and the fitting 264 are very small to reduce their thermal masses, the available space for grooves is likewise very small. Consequently, in some small-scale applications only two or three grooves may be able to fit in the available space. As the ferrule 100 becomes longer in other applications, more grooves are practical. When more space is available, the fabrication techniques and tool wear life may drive the decision of groove size and number.

Once a rough or preliminary design is completed in accordance with the considerations described above, the design may be validated using any suitable techniques. For example, the design may be modeled using an appropriate modeling tool such as, for example, finite element analysis (FEA) software. Physical prototypes based on the design may then be fabricated, and actual fluid seals may then be made using the prototypes and tested under both static and dynamic stresses. Using the modeling and experimental results, one or more design parameters (e.g., number of grooves, axial position and spacing of grooves, groove angle, etc.) may be adjusted as needed to provide the desired level of protection against over-compression. For example, if it is found that the grooves are not collapsing enough and the tube 262 is experiencing damage with the applied force, the groove thicknesses (T2, T3, etc.) may be reduced, and/or more grooves may be added, and/or other adjustments may be made.

Figure 3:
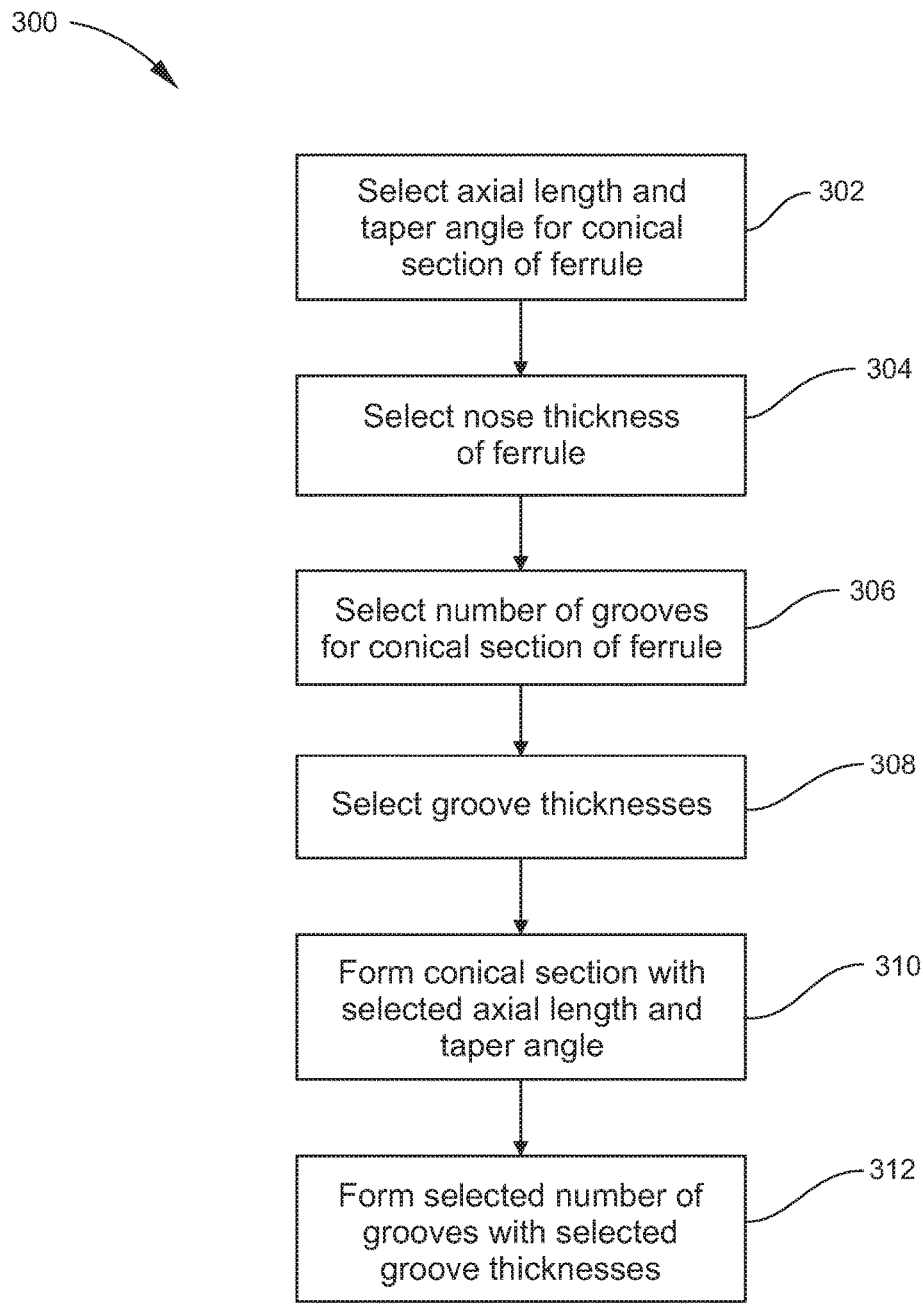
FIG. 3 is a flow diagram illustrating an example of a method for designing or fabricating a ferrule according to some embodiments.

An example of a method for designing (or fabricating) a ferrule such as the ferrule 100 described above will now be described with reference to FIG. 3, which is a flow diagram 300 illustrating examples of steps of the method. Generally, a ferrule designed according to the method includes a first end, a second end, an outside surface extending from the first end to the second end, and an inside surface defining a bore extending along a central axis from the first end to the second end. The ferrule further includes the conical section extending from the first end toward the second end. That is, the conical section extends for at least some portion of the total axial length of the ferrule, and may transition to a straight cylindrical section as described above. A portion of the outer surface in the conical section at or near the front end serves as a sealing region as described above. According to the method, one or more parameters relating to the configuration of the ferrule are selected. In the example illustrated in FIG. 3, an axial length and a taper angle are selected for the conical section (step 302). A nose thickness of the ferrule (i.e., the thickness between the inside surface and the sealing region, along a radial direction orthogonal to the central axis of the ferrule) is also selected (step 304). The number of annular grooves (typically two or more) to form on a portion of the outer surface located in the conical section are also selected (step 306). Further, a plurality of groove thicknesses of the ferrule at the respective grooves (i.e., the thickness between the inside surface and the root of each groove) is selected (step 308). The conical section is then formed so as to have the selected axial length and the selected taper angle, and such that the ferrule has the selected nose thickness (step 310). The selected number of grooves are formed in the conical section such that the ferrule has the groove thicknesses selected for the respective grooves (step 312). It will be understood that in addition or alternative to one or more of the parameters illustrated in FIG. 3, one or more other parameters may be selected such as groove angles and inter-groove spacing as described above. As also described above, various parameters may be selected based on one or more factors. It will also be understood that the order of steps as presented in FIG. 3, such as the order of selection steps 302 to 308, is merely one example and the order of steps may be rearranged as desired.

Figure 4:
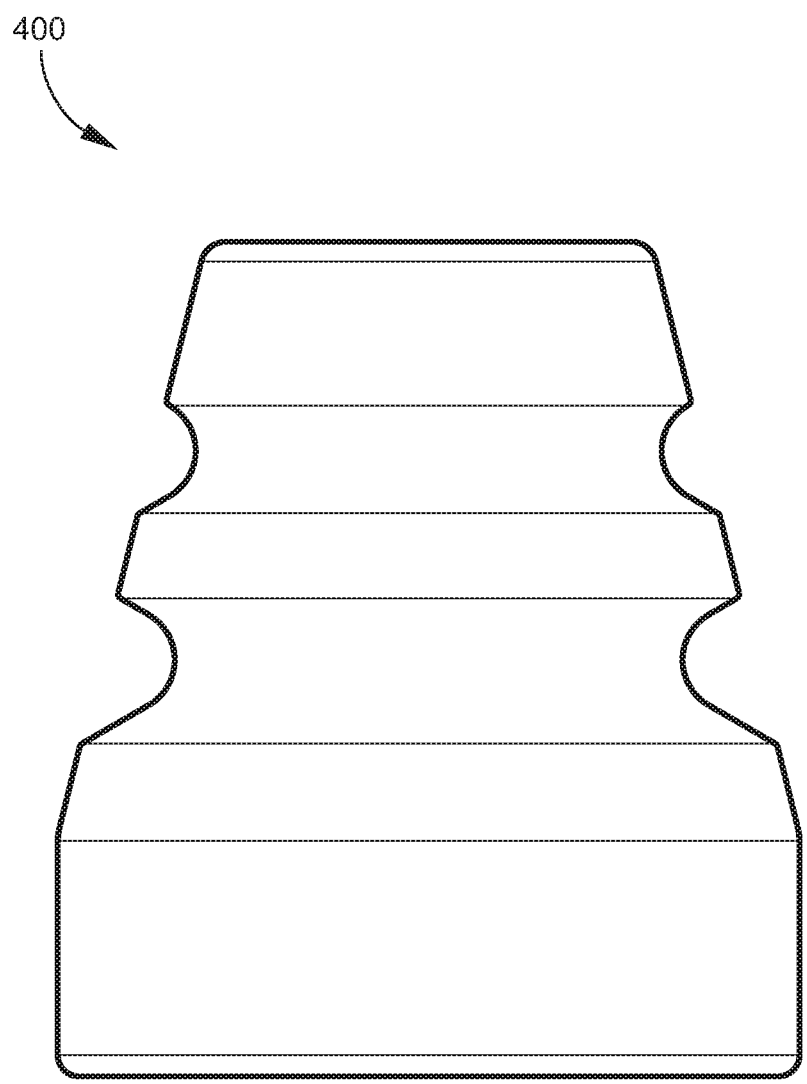
FIG. 4 is a side view of an example of a ferrule according to another embodiment.
Figure 5:
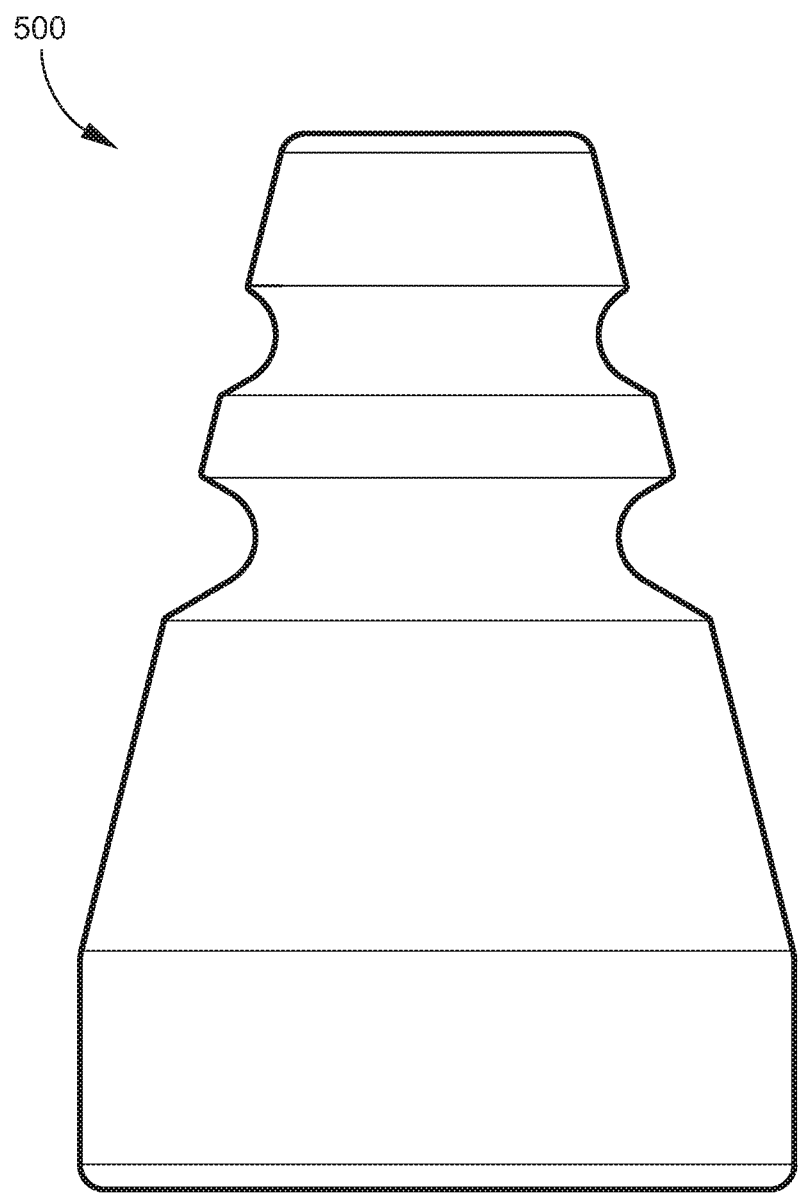
FIG. 5 is a side view of an example of a ferrule according to another embodiment.

It will be understood that the configuration (geometry, shape, etc.) of the ferrule 100 described above and illustrated in the Figures is but one example of how staged collapse zones or grooved regions may be implemented in a ferrule. Other variations and different geometries providing the same or similar effect are encompassed by the present disclosure. Moreover, more or less than three grooved regions may be provided as noted above. As a few non-limiting examples, FIG. 4 is a side view of an example of a ferrule 400 according to another embodiment in which the ferrule 400 has a two-groove configuration. FIG. 5 is a side view of another example of a ferrule 500 that has a two-groove configuration.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A ferrule, comprising:
   a first end surface;
   a second end surface spaced from the first end surface along a central axis;
   a lateral outside surface surrounding the central axis and extending from the first end surface to the second end surface, the lateral outside surface defining an outer radius of the ferrule along a radial direction orthogonal to the central axis; and
   an inside surface surrounding the central axis and extending from the first end surface to the second end surface, the inside surface defining a bore extending along the central axis and open at the first end surface and the second end surface, wherein:
   the ferrule comprises a conical section extending from the first end surface toward the second end surface, such that the outer radius increases in a direction away from the first end surface;
   the lateral outside surface comprises a sealing region at or near the first end surface, the sealing region being configured to form a sealing interface with a fitting in response to axial compression of the ferrule;
   the conical section comprises two or more collapse zones between the sealing region and the second end surface, the collapse zones being axially spaced from each other and from the sealing region,
   the ferrule has a thickness along the radial direction between the inside surface and the lateral outside surface, and the thickness at one or more of the collapse zones is greater than the thickness at the sealing region; and
   the sealing region and the collapse zones are configured to axially collapse in sequential order in response to axial compression of the ferrule, starting with the sealing region and followed by each successive collapse zone.

2. The ferrule of claim 1, wherein the thickness successively increases at each collapse zone in a direction away from the first end surface.

3. The ferrule of claim 2, wherein the thickness at each collapse zone is 10% to 50% greater than the thickness at the preceding collapse zone.

4. The ferrule of claim 1, wherein the lateral outside surface comprises a plurality of annular grooves, each annular groove located at a respective collapse zone, and wherein the annular grooves have respective groove thicknesses corresponding to the thickness of the ferrule at the respective collapse zones.

5. The ferrule of claim 4, wherein each annular groove has a groove angle selected from the group consisting of:
   each annular groove has a groove angle in a range from 30 to 90 degrees;
   the groove angle of each annular groove is the same as the groove angles of the other annular grooves; and
   the groove angle of at least one of the annular grooves is different from the groove angles of the other annular grooves.

6. The ferrule of claim 1, wherein the sealing region has a taper angle in a range from 20 to 90 degrees.

7. A fluidic seal assembly, comprising:
   the ferrule of claim 1;
   a tube disposed in the bore of the ferrule; and
   a fluidic fitting comprising an inside fitting wall surrounding the central axis and defining a fitting bore, wherein the ferrule is disposed in the fitting bore and the sealing region is in compressive contact between the inside fitting wall and the tube.

8. The fluidic seal assembly of claim 7, wherein the inside fitting wall has a tapered section in contact with the sealing region, and the tapered section has a taper angle greater than a taper angle of the sealing region.

9. The fluidic seal assembly of claim 8, wherein the taper angle of the tapered section is in a range from 30 to 120 degrees.

10. A method for forming a fluidic seal, the method comprising:
  inserting a tube in the bore of the ferrule of claim 1;
  inserting the ferrule in a fitting bore of a fitting, wherein the sealing region of the ferrule contacts an inside fitting wall of the fitting; and
  axially compressing the ferrule against the inside fitting wall in a direction along the central axis, wherein the sealing region collapses and creates a seal with the inside fitting wall and with the tube; and
  further axially compressing the ferrule against the inside fitting wall, wherein at least the collapse zone closest to the sealing region axially collapses.

11. The method of claim 10, wherein further axially compressing the ferrule axially collapses the collapse zone closest to the sealing region without further collapsing the sealing region.

12. The method of claim 10, wherein further axially compressing the ferrule axially collapses at least two collapse zones in sequential order, starting with the collapse zone closest to the sealing region.

13. A method for designing a ferrule, the ferrule comprising a first end, a second end, an outside surface extending from the first end to the second end, and an inside surface defining a bore extending along a central axis from the first end to the second end, the method comprising:
  selecting an axial length and a taper angle for a conical section of the ferrule, the conical section extending from the first end toward the second end;
  selecting a nose thickness of the ferrule, wherein the nose thickness is defined between the inside surface and a sealing region of the outside surface along a radial direction orthogonal to the central axis, the sealing region being located at or near the first end;
  selecting a number of annular grooves to form on the outer surface in the conical section, wherein the number is two or greater;
  selecting a plurality of groove thicknesses of the ferrule at the respective grooves, wherein each groove thickness is defined between the inside surface and the outside surface at the corresponding groove along the radial direction orthogonal to the central axis, and one or more of the groove thicknesses are greater than the nose thickness;
  forming the conical section such that the conical section has the selected axial length and the selected taper angle, and the ferrule has the selected nose thickness, wherein the conical section comprises two or more collapse zones between the sealing region and the second end; and
  forming the selected number of grooves in the conical section such that the ferrule has the groove thicknesses selected for the respective grooves,
  wherein the sealing region and collapse zones are configured to axially collapse in sequential order in response to axial compression of the ferrule.

14. The method of claim 13, wherein selecting nose thickness is based on a parameter selected from the group consisting of:
  a material of which the ferrule is composed;
  the taper angle;
  an inside diameter of a fitting with which the sealing region is to form a seal;
  an outside diameter of a tube with which the inside surface is to form a seal; and
  a combination of two or more of the foregoing.

15. The method of claim 13, wherein selecting the number of annular grooves is based on a parameter selected from the group consisting of:
  the axial length of the conical section;
  an axial spacing between the grooves;
  an axial spacing between the sealing region and the groove closest to the sealing region; and
  a combination of two or more of the foregoing.

16. The method of claim 13, comprising selecting an axial spacing between each groove and an axial spacing between the sealing region and the groove closest to the sealing region, such that the sealing region and the grooves collapse in the sequential order in response to the axial compression of the ferrule, starting with the sealing region and followed by each successive groove.

17. The method of claim 13, comprising selecting respective groove angles of the grooves.

18. The method of claim 17, wherein selecting the groove angles is based on a parameter selected from the group consisting of:
  the groove thicknesses;
  an axial spacing between the grooves;
  an axial spacing between the sealing region and the groove closest to the sealing region;
  a combination of two or more of the foregoing.

19. The method of claim 13, wherein the selecting a plurality of groove thicknesses of the ferrule at the respective grooves comprises selecting the groove thicknesses such that the groove thicknesses successively increase in a direction away from the sealing region.

20. A ferrule, comprising:
  a first end surface;
  a second end surface spaced from the first end surface along a central axis;
  a lateral outside surface surrounding the central axis and extending from the first end surface to the second end surface, the lateral outside surface defining an outer radius of the ferrule along a radial direction orthogonal to the central axis; and
  an inside surface surrounding the central axis and extending from the first end surface to the second end surface, the inside surface defining a bore extending along the central axis and open at the first end surface and the second end surface, wherein:
  the ferrule comprises a conical section extending from the first end surface toward the second end surface, such that the outer radius increases in a direction away from the first end surface;
  the lateral outside surface comprises a sealing region at or near the first end surface, the sealing region being configured to form a sealing interface with a fitting in response to axial compression of the ferrule;
  the conical section comprises two or more collapse zones between the sealing region and the second end surface, the collapse zones being axially spaced from each other and from the sealing region,
  the thickness successively increases at each collapse zone in a direction away from the first end surface; and
  the sealing region and the collapse zones are configured to axially collapse in sequential order in response to axial compression of the ferrule, starting with the sealing region and followed by each successive collapse zone.

* * * * *